US00PP17785P2

(12) United States Plant Patent
Misato et al.

(10) Patent No.: US PP17,785 P2
(45) Date of Patent: Jun. 5, 2007

(54) ***VERBENA* PLANT NAMED 'SUNVIVAHO'**

(50) Latin Name: *Verbena×hybrida*
Varietal Denomination: Sunivaho

(75) Inventors: Tomoya Misato, Shiga (JP); Naoto Takamura, Shiga (JP); Shutaro Tatsumi, Kanagawa (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/264,766

(22) Filed: Nov. 1, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Verbena* plant named 'Sunvivaho', characterized by its upright and outwardly spreading plant habit; vigorous and freely branching growth habit; dense and bushy plant form; white-colored flowers; freely and continuous flowering habit; long-lasting flowers; and good garden performance.

1 Drawing Sheet

Botanical designation: *Verbena×hybrida.*
Cultivar denomination: 'Sunvivaho'.

BACKGROUND OF THE INVENTION

The present Invention relates to a new and distinct cultivar of *Verbena* plant, botanically known as *Verbena×hybrida,* and hereinafter referred to by the cultivar name Sunvivaho.

The new *Verbena* is a naturally-occurring branch mutation of the *Verbena×hybrida* cultivar Sunvivabura, disclosed in U.S. Plant Pat. No. 13,725. The new *Verbena* was discovered and selected by the Inventors from a single flowering plant found within a population of plants of 'Sunvivabura' in a controlled environment in October 2002 in Higashiomi, Shiga, Japan.

Asexual reproduction of the new cultivar by terminal cuttings at Higashiomi, Shiga, Japan since October, 2004, has shown that the unique features of this new *Verbena* are stable and reproduced true to type in successive generations.

SUMMARY OF THE INVENTION

Plants of the cultivar Sunvivaho have not been observed under all possible environmental conditions. The phenotype may vary somewhat with variations in environment such as temperature and light level without, however, any variance in genotype.

The following traits have been repeatedly observed and are determined to be the unique characteristics of 'Sunvivaho'. These characteristics in combination distinguish 'Sunvivaho' as a new and distinct cultivar of *Verbena:*

1. Upright and outwardly spreading plant habit.
2. Vigorous and freely branching growth habit; dense and bushy plant form.
3. White-colored flowers.
4. Freely and continuous flowering habit.
5. Long-lasting flowers.
6. Good garden performance.

Plants of the new *Verbena* differ from plants of the parent, the cultivar Sunvivabura, in the following characteristics:

1. Plants of the new *Verbena* were shorter but broader than plants of the cultivar Sunvivabura.
2. Plants of the new *Verbena* had larger leaves and inflorescences than plants of the cultivar Sunvivabura.
3. Plants of the new *Verbena* and the cultivar Sunvivabura differed in flower color as plants of the cultivar Sunvivabura had light pink-colored flowers.

Plants of the new *Verbena* can be compared to plants of the cultivar Sunmariripi, disclosed in U.S. Plant Pat. No. 11,037. In side-by-side comparisons conducted in Yokaichi, Shiga, Japan, plants of the new *Verbena* differed from plants of the cultivar Sunmariripi in the following characteristics:

1. Plants of the new *Verbena* were more upright than plants of the cultivar Sunmariripi.
2. Plants of the new *Verbena* and the cultivar Sunmariripi differed in leaf shape.
3. Plants of the new *Verbena* and the cultivar Sunmariripi differed in flower coloration as plants of the cultivar Sunmariripi had pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Verbena.*

The photograph at the top of the sheet is a side perspective view of a typical plant of 'Sunvivaho'.

The photograph at the bottom of the sheet is a close-up view of typical inflorescences of 'Sunvivaho'.

DETAILED BOTANICAL DESCRIPTION

The aforementioned photographs, following observations and measurements describe plants grown in Higashiomi, Shiga, Japan in an outdoor nursery and under commercial production practices. Plants were grown in 15-cm containers and were about five months old when the photographs and description were taken. During the production of the plants, day temperatures averaged 23° C. and night temperatures averaged 13° C. Plants were pinched one time in the spring. In the following description, color references are made to The Royal Horticultural Society Colour Chart, 2001 Edition, except where general terms of ordinary dictionary significance are used.

Botanical classification: *Verbena×hybrida* cultivar Sunvivaho.

Parentage: Naturally-occurring branch mutation of the *Verbena×hybrida* cultivar Sunvivabura, disclosed in U.S. Plant Pat. No. 13,725.

Propagation:

*Type.*—By terminal cuttings.

*Time to initiate roots.*—About 10 to 14 days at 20° C. to 25° C.

*Time to produce a rooted plant.*—About one month at 20° C. to 25° C.

*Root description.*—Fine, fibrous, fleshy; ivory to pale brown in color.

*Rooting habit.*—Freely branching.

Plant description:

*Plant form/habit.*—Upright and outwardly spreading plant habit; broadly inverted triangle; vigorous growth habit. Freely branching habit with about 35 lateral branches per plant; dense and bushy plant form.

*Plant height.*—About 14.2 cm.

*Plant width* (*spread*).—About 63.8 cm.

*Lateral branches.*—Length: About 28 cm. Diameter: About 3 mm. Internode length: About 3 cm. Strength: Moderately strong. Texture: Pubescent. Color: 144B.

*Foliage description.*—Arrangement: Opposite, simple. Length: About 5.6 cm. Width: About 3.6 cm. Shape: Hastate. Apex: Acute. Base: Truncate. Margin: Serrate. Texture, upper and lower surfaces: Pubescent; coarse. Venation pattern: Pinnate; reticulate. Color: Developing and fully expanded leaves, upper surface: 137A; venation, close to 145C. Developing and fully expanded leaves, lower surface: 146A; venation, close to 145C. Petiole length: About 4 mm. Petiole diameter: About 1.5 mm. Petiole texture, upper and lower surfaces: Pubescent. Petiole color, upper and lower surfaces: 145C.

Flower description:

*Flower type/habit.*—Single, star-shaped salverform flowers arranged in umbels; flowers face mostly upright. Freely flowering habit with inflorescences per plant each with about twelve open flowers each.

*Fragrance.*—None detected.

*Natural flowering season.*—Continuously flowering from spring to late autumn in Japan. Flowers not persistent.

*Postproduction longevity.*—Flowers last about one week on the plant.

*Inflorescence height.*—About 2.9 cm.

*Inflorescence diameter.*—About 5.6 cm.

*Flower buds.*—Height: About 1.5 cm. Diameter: About 2.2 mm. Shape: Cylindrical. Color: N155D.

*Flowers.*—Diameter: About 2.1 cm. Depth: About 2.3 cm.

*Petals.*—Quantity per flower: Typically five in a single whorl; petals fused at the base into a narrow tube. Lobe length: About 9.1 mm. Lobe width: About 8.8 mm. Shape: Cordate. Apex: Emarginate. Margin: Entire. Texture, upper and lower surfaces: Smooth, glabrous; velvety. Color: Developing and fully expanded petals, upper surface: 155D. Developing and fully expanded petals, lower surface: 155D.

*Sepals.*—Quantity per flower: Typically five in a single whorl, fused; narrow tubular calyx. Length: About 9 mm. Width: About 0.9 mm. Shape: Lanceolate. Apex: Acute. Texture, upper and lower surfaces: Smooth, glabrous. Color, upper and lower surfaces: 144A.

*Peduncles.*—Length: About 2.5 cm. Diameter: About 1.1 mm. Texture: Pubescent. Color: 144B.

*Reproductive organs.*—Stamens: Quantity per flower: Typically four. Anther shape: Ellipsoidal. Anther length: About 0.4 mm. Anther color: 150B. Pollen amount: Scarce. Pollen color: 10D. Pistils: Quantity per flower: Typically one. Pistil length: About 1.6 cm. Stigma shape: Bi-parted. Stigma color: 144A. Style length: About 1.4 cm. Style color: 149C. Ovary color: N144C.

*Seed/fruit.*—Seed and fruit development have not been observed.

Disease/pest resistance: Plants of the new *Verbena* have not been noted to be resistant to specific pathogens and pests common to *Verbena*.

Garden performance: Plants of the new *Verbena* have been observed to have good garden performance and tolerate rain, wind and tolerated temperatures from about 0° C. to 35° C.

It is claimed:

1. A new and distinct cultivar of *Verbena* plant named 'Sunvivaho', as illustrated and described.

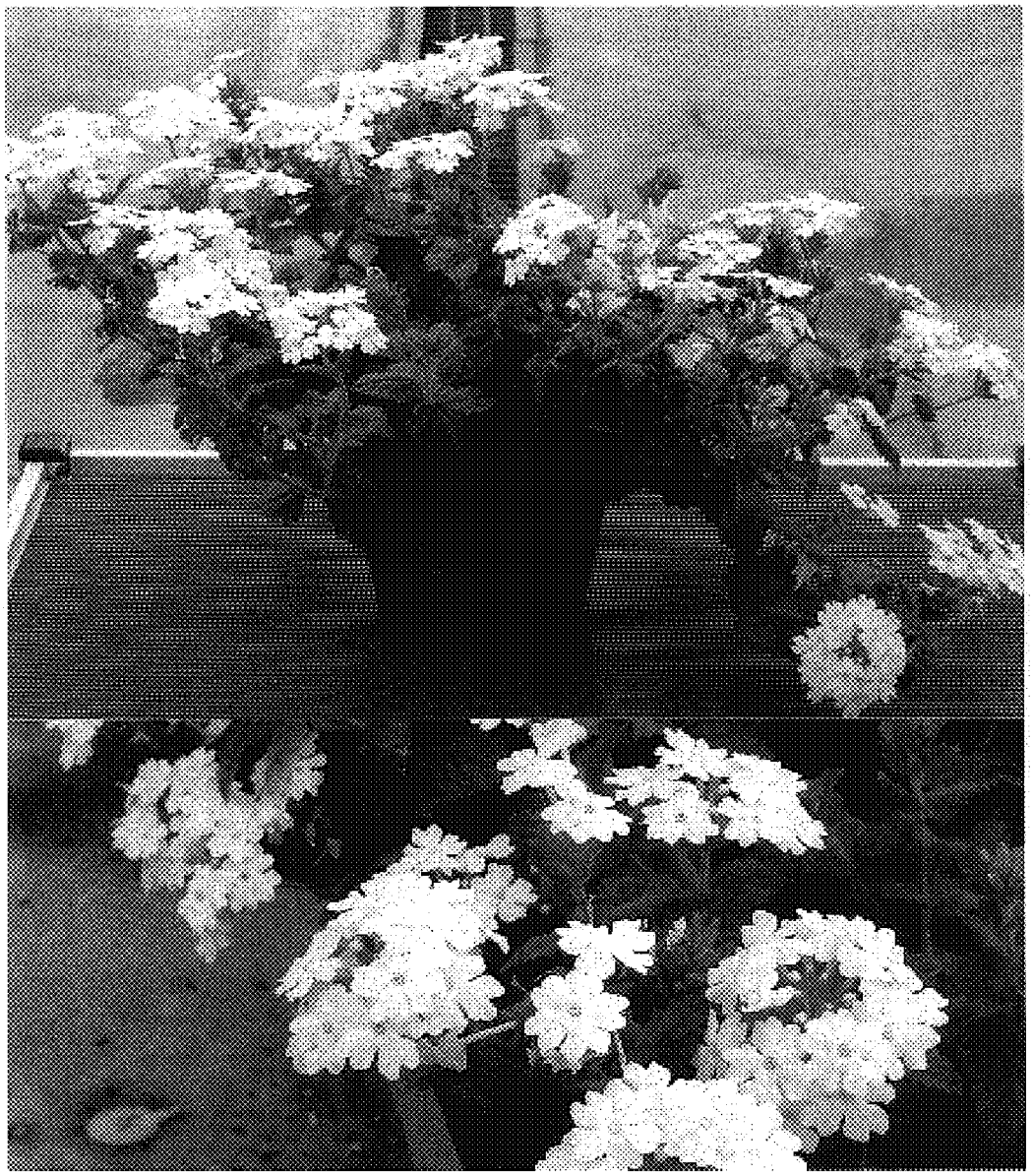

* * * * *